United States Patent [19]
Sanfilippo et al.

[11] Patent Number: 5,856,585
[45] Date of Patent: *Jan. 5, 1999

[54] PROCESS OF CATALYTIC PARTIAL OXIDATION OF NATURAL GAS IN ORDER TO OBTAIN SYNTHESIS GAS AND FORMALDEHYDE

[75] Inventors: Domenico Sanfilippo, Paullo; Luca Basini; Mario Marchionna, both of Milan, all of Italy

[73] Assignee: Snamprogetti S.p.A., Milan, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 286,978

[22] Filed: Aug. 8, 1994

[30] Foreign Application Priority Data

Aug. 27, 1993 [IT] Italy .................. MI93A1857

[51] Int. Cl.$^6$ .................................... C07C 45/00
[52] U.S. Cl. .................. 568/470; 568/909; 560/475; 252/373
[58] Field of Search .................... 568/470, 909; 560/475; 252/373

[56] References Cited

U.S. PATENT DOCUMENTS 5,149,464  9/1992  Green et al. .................. 252/373
5,336,655  8/1994  Basini et al. .

FOREIGN PATENT DOCUMENTS 0 303 438  2/1989  European Pat. Off. .
2 239 406  7/1991  United Kingdom .

OTHER PUBLICATIONS

Ullman's Encyclopedia of Industrial Chemistry, Carbon Monoxide, vol. A5, Henry LEDON, "Carbon Monoxide", 9.2 'Production of Organic Chemicals, pp. 211–213, 1986.

Applied Catalysis, B 1, J.K. Hochmuth, "Catalytic Partial Oxidation of Methane Over A Monolith Supported Catalyst", 1992, pp. 89–100 plus title page.

Catalysis Letter 6, Patrick D.F. Vernon, et al., "Partial Oxidation of Methane to Synthesis Gas", 1990, pp. 181–186.

Primary Examiner—Marianne M. Cintins
Assistant Examiner—Dwayne C. Jones
Attorney, Agent, or Firm—Oblon, Spivak, McClelland, Maier & Neustadt, P.C.

[57] ABSTRACT

Process of catalytic partial oxidation of natural gas in order to obtain synthesis gas and formaldehyde, integrated with processes of hydrogenation of the resulting CO, such as Fischer-Tropsch and methanol syntheses. Such an oxidation is carried out by means of a catalyst constituted by one or more compounds of metals form Platinum Group, which is given the shape of wire meshes, or is deposited on a carrier made from inorganic compounds, in such a way that the level of metal or metals from Platinum Group, as percent by weight, is comprised within the range of from 0.1 to 20% of the total weight of catalyst and carrier, by operating at temperatures comprised within the range of from 300° to 950° C., under pressures comprised within the range of from 0.5 to 50 Atm, at space velocities comprised within the range of from 20,000 to 1,500,000 h$^{-1}$.

6 Claims, 1 Drawing Sheet

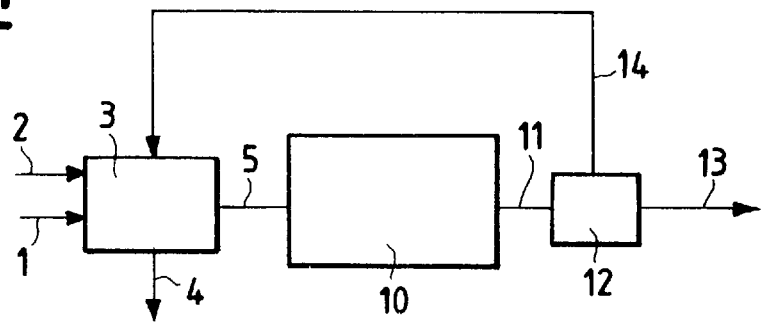
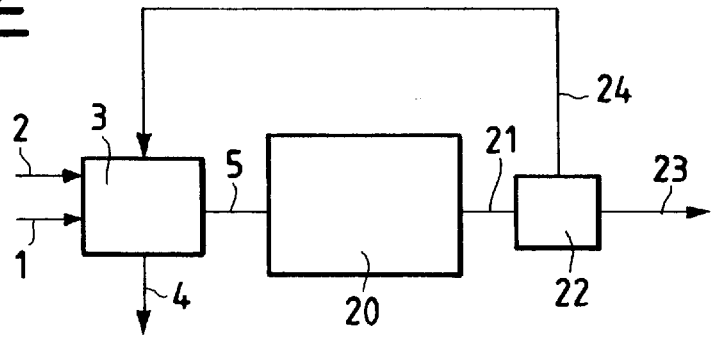
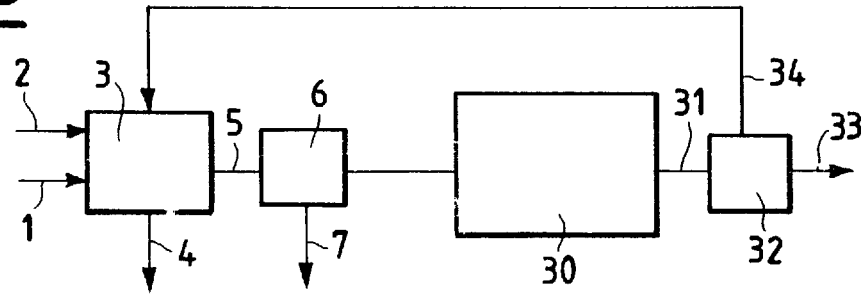

PROCESS OF CATALYTIC PARTIAL OXIDATION OF NATURAL GAS IN ORDER TO OBTAIN SYNTHESIS GAS AND FORMALDEHYDE

The present invention relates to a catalytic partial oxidation process (which in the present patent application will be referred to, briefly, as "CPO") of natural gas in order to obtain synthesis gas and formaldehyde; more particularly, it relates to the production of synthesis gas for Fischer-Tropsch (F-T) processes, to processes for methanol and methanol-dimethylether mixtures synthesis under conditions of high conversion rate per pass.

The synthesis gas is presently manufactured by means of processes of steam reforming, autothermal reforming, non-catalytic partial oxidation of hydrocarbons. The steam reforming processes catalytically convert mixtures of hydrocarbons and steam ($H_2O/C=2.5-3.5$ by vol/vol) into mixtures of CO and $H_2$ with a $H_2/CO$ ratio typically of round 3 when the process is carried out by starting from natural gas. The main reactions which describe the process are $$C_nH_m + nH_2O \longrightarrow nCO + (m+n/2)H_2 \quad [1]$$

$$H_2O + CO \longrightarrow CO_2 + H_2 \quad [2]$$

The $H_2O:C$ ratio in the reactant mixture is determined by the temperature and pressure conditions under which the reactions are carried out, as well as by the need for inhibiting the coal formation reactions [3] and [4]:

$$C_nH_m \longrightarrow C_n + m/2\, H_2 \quad [3]$$

$$2CO \longrightarrow C + CO_2 \quad [4]$$

The commonly used catalysts in this process are based on Ni supported on Al, Mg, Si oxide carriers. The used carriers display high thermal stability and mechanical strength characteristics. The reactions take place inside tubular reactors contained inside a combustion chamber. The pressures inside the tubes are typically comprised within the range of from 1 to 5 MPa, and the temperature at tube outlets is typically higher than 850° C. (see, e.g., Catalysis Science and Technology" Vol. 5, Chapter 1, J. R. Rostrup-Nielsen). The stay times of the gas streams inside the interior of the catalytic beds are of round five seconds. Along the reforming tubes (which are approximately 15-m long), which are totally filled with catalyst, large gradients arise in the gas mixture composition.

The processes of non-catalytic partial oxidation are less widely used and are employed in order to convert mixtures of hydrocarbons, oxygen, steam and air into synthesis gas with $H_2/CO$ ratios of typically round 2 if one starts from natural gas. The process chemistry can be represented by means of equations [5] and [2]

$$C_nH_m + n/2\, O_2 \longrightarrow nCO + m/2\, H_2 \quad [5]$$

The facilities installed to date by Texaco and Shell (see Hydrocarbon Processing; April 1990, p. 99) are provided with adiabatic reactors in which the reactions are started inside the reactors by means of a burner in which the reactions of total combustion [6] of hydrocarbons $$C_nH_m + (n+m/2)O_2 \longrightarrow n\, CO_2 + m/2\, H_2O \quad [6]$$

mainly take place.

These reactions produce large amounts of heat, steam and $CO_2$. Heat causes cracking reactions of unburnt hydrocarbons to take place, and favours the reaction of steam- and $CO_2$-reforming [1], [7]

$$nCO_2 + C_nH_m \longrightarrow 2nCO + m/2\, H_2 \quad [7]$$

The process temperatures are typically comprised within the range of from 1250° to 1500° C. and pressure is caused to range from 3 to 12 MPa. The process requires very short stay times of the reactant/product mixture inside the reactor (of about 0.5 seconds). As in the reactant mixtures ratios of $O_2:CH_4$ are used which are normally larger than 0.6 (by vol/vol), the produced syn gas contains large amounts of $CO_2$.

The autothermal reforming processes are carried out inside adiabatic reactors to which mixtures of hydrocarbons, oxygen and steam are fed; also in this case, the $O_2:CH_4$ ratios are larger than the stoichiometric value of 0.5. In a first reaction zone, by means of a burner the total combustion reactions of hydrocarbons [6] are started, in a second reaction zone, inside a catalytic bed the steam [1] and $CO_2$ reforming [7] reactions take place. In the catalytic bed, catalysts are used which display similar characteristics to those as described above for steam reforming processes. From autothermal reforming, synthesis gas mixtures are obtained with intermediate $H_2:CO$ ratios between those found in syn gas from steam reforming and non-catalytic partial oxidation, respectively. The reactor outlet temperature is typically comprised within the range of from 900° to 1000° C., but the temperature inside the zone in which the burner is installed is considerably higher. The internal reactor pressure is comprised within the range of from 2 to 4 MPa. The stay times inside the catalytic bed are of round 0.7 seconds.

Synthesis gas is mainly used in F-T syntheses in order to obtain hydrocarbon blends, in methanol synthesis, in ammonia synthesis.

F-T processes have been mainly realized by Sasol in South Africa and use synthesis gas produced from coal by means of a coal gasification and methane reforming process. The investment costs for the Sasol facilities are subdivided as follows (see M. E. Dry "The Fischer-Tropsch synthesis—Commercial aspects" Catal. Today, 1990, 6, 183):

coal mining, steam and $O_2$ production 47% synthesis gas production 23%

F-T synthesis 30%

As one may see, the coal mining and conversion costs and the syn gas production costs constitute approximately 70% of total process costs and producing fuels from coal is economically feasible if one has available coal at much lower costs than of petroleum. The syn gas mixtures obtained from Sasol processs contain $H_2:CO$ ratios comprised within the range of from 1.7 to 2.

F-T synthesis mainly produce hydrocarbons according to equation [8]

$$2nH_2 + nCO \longrightarrow CnH_{2n} + nH_2O \quad [8]$$

In reality, F-T synthesis is a process of polymerization of $C_1$ units in which saturated and unsaturated, straight and branched-chain hydrocarbons are produced.

In general, the presently available technologies of hydrogenation of carbon monoxide downstream from the steam reforming, autothermal reforming, partial oxidation processes require that methane levels are lower than 5%. The reactions of hydrogentaion of carbon monoxide with mixtures of pure CO and $H_2$ display lower conversion rates than 70%. low levels of methane in synthesis gas are necessary in order to increase the partial pressures of CO and $H_2$ and prevent kinetic and thermodynamic constraints from causing the conversion rates, experienced in CO hydrogenation reactions, to decrease. A decrease in conversion rate implies an increase in the amounts of reactants to be recycled and $CH_4$ accumulating during the recycles.

Owing to these reasons, the target is values of methane conversion rate higher than 95%. Since 1985, processes for the synthesis of diesel fuels from natural gas have been developed, which are based on an intermediate syn gas production, a F-T synthesis of long-chain hydrocarbons, and a hydrocracking of the latter. In this case too, the step of syn gas production contributes for approximately 60% to total production costs.

Also in conventional methanol production processes, at temperatures comprised within the range of from 220° to 300° C., the syn gas production costs contribute with similar percent amounts.

Therefore, in F-T syntheses and in methanol syntheses by means of the conventional routes, synthesis gas mixtures are use which contain negligible levels of methane in order to prevent that a decrease in $H_2$ and CO partial pressure may cause both a decrease in reaction rates and consequently in conversion rates per pass, and methane accumulating in the recycled gas to the synthesis step.

On the contrary, the methanol syntheses with high conversion rates per passage, operating at low temperatures, are capable of converting approximately 90% of synthesis gas into methanol even in the presence of large amounts of inert gases. However, in this case, $CO_2$ and $H_2O$ impurities are not tolerated in the reactant mixtures.

This process was mainly studied by Shell (EP-285 228; EP-287 151; EP-289 067; EP-306 113; EP-306 114; EP-309 047; EP-317 035), Brookhaven National laboratories (U.S. Pat. No. 4,935,395; U.S. Pat. No. 4,614,749; U.S. Pat. No. 4,623,634; U.S. Pat. No. 4,613,623), Mitsui (JP-81/169 934; JP-82/128 642), Sintef (WO-86/3190), Snamprogetti (IT 20,028 A/88; IT 23,101 A/88; IT 23,102 A/88; IT 22,352 A/89; EP 357 071, EP-504 981).

The catalytic systems which are used in these syntheses contain nickel [$Ni(CO)_4$/MeONa] or copper (CuCl/MeONa, copper chromite/MeONa) and the syntheses are carried out in slurry reactors. The reactions take place at temperatures comprised within the range of from 90° to 120° C. and the pressures are comprised ithin the range of from 5 to 50 atm. Under these conditions, conversion rates of round 90% and selectivities higher than 95% are obtained by using CO and $H_2$ mixtures (with $H_2$:CO ratios=2 by vol/vol) and high levels of such inert molecules as nitrogen and methane (typically, reactions were studied in which the inerts levels were of approximately 40%).

Also the syntheses of methanol-dimethyl ether mixtures can be carried out with high values of conversion per pass, because the formation of dimethyl. ether with consequent methanol shift favours the obtainment of total conversions of $CO/H_2$ mixture [J. Bogild Hansen, F. Joensen—Stud. Surf. Sc. Catal., 61 (1991), 457]. Therefore, also in this case, the reaction can be carried out in the presence of such an inert gas as non-converted methanol.

It has now been found a process of catalytic partial oxidation (CPO) of natural gas to yield synthesis gas, using a noble metal containing catalyst, carried out at ultra high space velocity (UHSV), at considerably lower temperatures than as presently used and with even particularly low $O_2$:C and $H_2O$:$CH_4$ molar ratios, which process can be strongly integrated with processes of carbon monoxide hydrogenation, such as F-T syntheses and methanol or methanol-dimethyl ether mixtures synteses.

Formaldehyde is a byproduct from the present process and is separated before using syn gas when formed in relatively large amounts, e.g., in larger amounts than about 3% by weight.

The possibility of operating at higher space elocities (1,500,000>GHSV>20,000 $h^{-1}$) than has presently used (GHSV<10,000 $h^{-1}$) makes it possible small size reactors to be used, thus allowing savings to be accomplished in investment costs. The possibility of operating with reactant streams with molar ratios of $O_2$:$CH_4$<0.5 (by vol/vol), makes it possible the energy consumptions and the investment costs for oxygen production units, to be decreased.

The processes of catalytic partial oxidation of methane [12], carried out at lower space velocities than 15,000 $h^{-1}$, can be described as the sum of total hydrocarbon combustion [9] and steam and CO2 reforming reactions [10]–[11]

  [9]

  [10]

  [11]

  [12]

At lower temperatures than 600° C., the total oxydation reaction [9], strongly exothermic, is considerably favoured, whilst the steam and $CO_2$ reforming reactions [10]–[11], strongly endothermic, are unfavoured. On the contrary, at higher temperatures than 750° C., both these latter reactions are capable of converting $CO_2$ and $H_2O$ into synthesis gas.

The catalysts used in the CPO step according to the present invention makes it possible the reactions to be carried out with $O_2$:$CH_4$ ratios lower than 0.5 also in the absence of steam, under conditions which at present can not be used with the catalysts known from the prior art, owing to the coal formation reactions [3] and [4]. The synthesis gas produced under these conditions may contain even large amounts (of up to 50%) of unreacted methane and can be used in synthesis reactions with high conversion rate values per pass.

The influence of the high value of space velocity is reported in published studies by D. A. Hickman and L. D. Schmidt (Science 1993, 259, 343), which made experiments at higher temperatures than 1000° C. with rhodium-based catalysts, and by V. R. Choudari, A. S. Mamman, S. D. Sansare (Angew. Chem. Int. Ed. Engl. 1992, 31, 1189), which performed experimental tests at temperatures comprised within the range of from 300° to 900° C., with catalysts not constituted by noble metals (Fe, Co, Ni). The experimental tests disclosed in the present patent application are anyway different from those reported in published papers. The above Authors used different catalysts from those we studied, and consequently were unable to operate with $O_2$:$CH_4$ ratios<0.5 (by vol/vol) in order to avoid the coal formation reactions [3], [4] and did not obtain HCHO; furthermore, the CPO process according to the present invention enables synthesis gas to be produced under UHSV conditions even in the presence of large amounts of $CO_2$. The possibility of using $CO_2$ in the reactant mixture makes it possible considerable advantages to be gained whenever syn gas mixtures with $H_2$:CO ratios lower than 2 (by vol/vol) must be obtained. Such low values of said ratio are advantageous for producing long-chain and high-molecular-weight hydrocarbon in F-T syntheses. As we already briefly mentioned, long-chain hydrocarbon products can be converted into diesel fuels for engines for motor vehicles.

At the high space velocity values used in the CPO process according to the present patent application, the selectivity characteristics of CPO reactions are meaningfully changed. Carbon monoxide and hydrogen are produced with extremely high selectivity values even at low temperatures. The catalysts used in the experimental studies on CPO disclosed in the present patent application are considerably different from those reported in technical papers, because they may contain decidedly low levels of noble metal (down to 0.1%).

The syn gas production reactions are thought to be representable as follows:

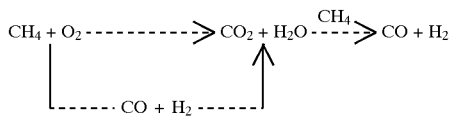

According to presently current opinions, people think that under high space velocity conditions, the primary products from oxidation reactions CO and $H_2$ may be obtained, which are then rapidly removed from catalyst surface before reacting to form the secondary reaction products.

The process of catalytic partial oxidation of natural gas in order to obtain synthesis gas and formaldheyde, the first object of the present invention, is characterized in that such an oxidation is carried out by means of a catalyst constituted by one or more compounds of metals from Platinum Group, which are given the shape of wire meshes, or are deposited on a carrier made from inorganic compounds, in such a way that the percent level of metal or metals from Platinum Group, by weight, is comprised within the range of from 0.1 to 20%, preferably of from 0.1 to 5% of the total weight of catalyst and carrier, by operating at temperatures comprised within the range of from 300° to 950° C., preferably of from 350° to 850° C., under pressures comprised within the range of from 0.5 to 50 atm, preferably of from 1 to 40 atm, at space velocities comprised within the range of from 20,000 to 1,500,000 $h^{-1}$, preferably of from 100,000 to 600,000 $h^{-1}$.

The used catalysts are particularly active as regards the CPO reactions, and are particularly inert as regards the coal formation reactions [3], [4] and are even capable of working with $O_2:CH_4$ ratios lower than 0.5 (by vol/vol), and in the presence of $CO_2$ without undergoing deactivation. In those cases when the ratio of $O_2:CH_4$ is lower than 0.5, in the CPO reactor leaving streams high contents of unreacted methane will be obtained.

If the CPO reactions are carried out by using reactants mixtures with ratios of $O_2/CH_4=0,65$ (by vol/vol), the methane content in leaving streams can be reduced down to levels which may even be lower than 5%.

As already briefly mentioned, CPO catalysts are used which contain metats from Platinum Group, in pellet form, prepared according to procedures disclosed in patent literature (UK Patent No. 2 240 284, UK Publ.No.2247465, IT-MI92A 001953, UK Publ. No. 2274284). Furthermore, in the CPO step, noble metals wire meshes can be used which are similar to those as used in nitric acid production, but with a higher Rh content than 9% by weight, or, still, enbloc catalysts. In particular in the latter case, in the present patent application an original method for preparing enbloc catalysts is disclosed, which makes it possible the noble metals to be rapidly deposited with a high dispersion degree, onto the surface of the monolithic body, by dipping the latter in an organic solution of organometallic Rh, Ru, Ir clusters. The metals get fixed on the surfaces of the monolithic body through a. solid-liquid reaction between the reactive surface sites and the organometallic clusters, which then undergo decomposition, until monoatomic species in an extremely highly dispersed state are produced. This procedure is substantially different from the impregnation processes, because the noble metal content which is fixed onto the carrier is determined by the number of active sites present on the surface of the latter.

A further object of the present invention are the integrated processes for methanol or methanol-dimethyl ether syntheses and for F-T syntheses.

The integrated process for methanol synthesis from synthesis gas essentially consists in causing the synthesis gas obtained by means of the process disclosed hereinabove, after the preliminary possible separation of formed formaldehyde, to react, by means of a suitable catalyst, by operating, in the case of the high-conversion-per-pass synthesis, after additionally separating $CO_2$ and $H_2O$ from said synthesis gas, at a temperature which is higher than 40° C. and lower than 200° C. and under a higher pressure than 1 MPa; or, in the case of the syntheses carried out by the conventional route, at a temperature higher than 200° C. and lower than 350° C., and under a higher pressure than 0.3 MPa.

The integrated process for the synthesis of methanol-dimethyl ether mixtures consists in causing the mixture of synthesis gas and methane, obtained as disclosed hereinabove, after the preliminary possible separation of any possibly formed formaldehyde, to react, in the presence of catalysts capable of producing methanol and of converting the so produced methanol into dimethyl ether, by operating at a temperature higher than 150° C. and lower than 400° C. and under a pressure higher than 0.1 MPa and lower than 10 MPa.

The integrated process for F-T syntheses from synthesis gas essentially consists in causing the synthesis gas obtained by means of the process as disclosed hereinabove, after the preliminary separation, if so desired, of any possibly formed formaldehyde, to react, by operating, in the presence of a suitable catalyst, at a temperature higher than 200° and lower than 400° C. and under a higher pressure than 1 MPa.

The presence of methane in the reactants mixture is presently allowed only if processes with high conversion rates per pass are used.

The considerable reduction in costs which can be accomplished in the syn gas production process makes it possible advantageous integrated processes for converting natural gas into liquid hydrocarbon and/or oxygen containing products via syn gas containing higher methane levels than 5% by volume, to be defined.

BRIEF DESCRIPTION OF DRAWINGS

In the accompanying FIGS. 1, 2 and 3 the above mentioned integrated processes are schematically shown.

In FIG. 1, the schematic is shown of the integrated process for F-T syntheses from natural gas via syn gas obtained by means of the process according to the present invention.

Natural gas (1) and oxygen (2) are fed to the reactor (3) in which the catalytic partial oxidation of natural gas takes place, with synthesis gas and formaldehyde being obtained.

Formaldehyde (4) can be separated from synthesis gases (5), which are fed to reactor (10) in which the F-T syntheses take place.

The effluent product (11) is sent to a separation unit (12) from which a stream (13) containing hydrocarbons with 2, or more than 2, carbon atoms, and water; and a stream (14), containing methane and hydrocarbons with 2, or less than 2, carbon atoms are obtained, with the latter being recycled to reactor (3).

In FIG. 2 the schematic is displayed of the integrated process for the synthesis of methanol or of methanol-dimethyl ether mixtures from natural gas via syn gas.

Natural gas (1) and oxygen (2) are fed to the reactor (3) in which the catalytic partial oxidation of natural gas takes place, with synthesis gas and formaldehyde being obtained.

Formaldehyde (4) can be separated from synthesis gases (5) which are fed to reactor (20) in which the syntheses of methanol or of methanol-dimethyl ether mixtures takes place.

The leaving product (21) is sent to a separation unit (22) from which a stream (23) containing methanol and oxygen-containing products; and a stream (24), containing methane and hydrocarbons with 2, or less than 2, carbon atoms are obtained, with the latter being recycled to reactor (3).

In FIG. 3, the schematic is shown of the integrated process for methanol synthesis under high conversions-rate-per pass conditions, from natural gas via syn gas.

Natural gas (1) and oxygen (2) are fed to the reactor (3) in which the catalytic partial oxidation of natural gas takes place, with synthesis gas and formaldehyde being obtained.

Formaldehyde (4) can be separated from synthesis gases (5) which, after being separated in (6) from $CO_2$ and $H_2O$ (7), are fed to reactor (30) in which the methanol synthesis takes place.

The effluent product (31) is sent to a separation unit (32), from which a stream (33) essentially containing methanol; and a stream (34) containing methane—which is recycled to reactor (3)—are obtained.

The cheapness of these processes is favoured by the possibility of separating from the end reaction products, and recycling to CPO unit, any unreacted light ($C_1$ and $C_2$) hydrocarbons.

In greater detail, the integrated process for synthesis gas production and use may employ, in CPO unit, mixtures of natural gas and oxygen or enriched air with molar ratios of $O_2/CH_4$ which may even be lower than 0.5, even in the absence of steam. The CPO process according to the present invention can also use, under UHSV conditions (ultra-high space velocity), $CH_4/O_2/CO_2$ mixtures not containing steam. The process conditions are such that oxygen will be totally converted in the syn gas production unit, whilst meaningful amounts of methane may remain in the effluent stream from CPO reactors, in particular when the ratio of $O_2:CH_4$ is lower than 0.5.

The CPO reaction products are mainly constituted by mixtures of $H_2$, CO, and $CH_4$ with small amounts of $H_2O$ and $CO_2$, with HCHO being a reaction byproduct. After separating formaldehyde, which can be recycled to the catalytic partial oxidation step, the CO and $H_2$ containing mixtures are used for synthetizing methanol and/or dimethyl ether (DME) and/or hydrocarbons.

In the event when in the effluent streams leaving the syn gas preparation unit, large amounts remain of unreacted methane, the latter remains as an inert substance during the subsequent step of synthesis of hydrocarbons and/or oxygen containing products, is more easily separated from the heavier reaction products and is recycled to the CPO unit.

These results are very difficult to reach under high pressure conditions: on the contrary, it has surprisingly been found that, by means of such processes as disclosed hereinabove, reactions and variations in selectivity rates can be obtained under superatmospheric pressure. If the production of synthesis gas under UHSV conditions is dedicated to methanol synthesis with high values of conversion rate per passage, reaction conditions will be used in which all oxygen is consumed and $CO_2$ and $H_2O$ present in synthesis gas will be removed before the hydrogenation step.

The results obtained from the experimental tests disclosed in the following examples show that the catalytic system for the CPO reaction can be described by means of equation [12] without water and carbon dioxide being produced as intermediate products by reaction [9] within a wide range of experimental conditions. In this way, high conversion rates can be obtained under low temperature and high space velocity conditions, because reaction [12] is very fast and is thermodinamically favoured within a wide temperature range (its equilibrium constant is of round $10^{16}$ within a temperature range of from 25° to 800° C.), whereas rections [10] and [11] are low and thermodinamically unfavoured at lower temperatures than 750° C. The high yields of synthesis gas which are obtained even at low temperatures when mixtures of $CH_4$ and $O_2$ with ratios of $O_2:CH_4<0.5$ (by vol/vol) are used, render particularly advantageous the reactions of methanol or methanol-dimethyl ether mixtures production carried out by means of the high conversion-rate-per-pass processes.

Some examples are now supplied in order to better illustrate the invention, it being anyway understood that the invention is not limited to them, or by them.

EXAMPLE 1

The CPO reactions and methanol synthesis at high values of conversion rate per pass from the resulting mixtures of synthesis gas and methane were carried out inside two reactors, at a pressure of 1.5 MPa.

In reactor "A" the CPO reactions were carried out at a temperature of 750° C. and with a GHSV value of 300,000 $h^{-1}$. The stream of hot gases leaving the first reactor at the temperature of 750° C. is cooled by means of a coil inside which a water stream flows and is sent (after removing small amounts of steam and $CO_2$ produced during CPO synthesis) to reactor "B" kept at the temperature of 100° C., in which methanol synthesis takes place.

The mixture of reaction products was analyzed both at first reactor outlet, and at second reactor outlet, in both cases by gas chromatography.

The reactor inside which the CPO reactions are carried out is constituted by a ceramic alumina tube surrounded by a steel cylinder. The alumina tube secures the chemical inertness of the reactor walls. and the steel tube constitutes the strong body which enables the experimental tests to be carried out at higher than atmospheric pressures.

The reaction gas, constituted by $CH_4$ and $O_2$ ($O_2:CH_4=$ 0.2:0.8 by vol/vol), flows through the catalytic bed (A) containing 0.5 g of an Rh- and Ru-based catalyst, with a contact time of $10^{-2}$ seconds (GHSV 300,000 $h^{-1}$).

The noble metals were deposited on a carrier constituted by silica-grafted alpha-alumina. Rh and Ru constitute 0.5% and 1%, respectively, by weight, of the material. The carrier (silica-grafted alumina) was prepared by means of condensation reactions between the reactive groups on alumina surface and tetraethyl silicate (TES), followed by hydrolysis and calcination. The noble metals were deposited by using hydrocarbonaceous solutions of $Rh_4 (CO)_{12}$ and $Ru_3 (CO)_{12}$, according to such procedures as disclosed in UK Patent No. 2 240 284, UK Publ. No. 2247465, IT-MI92 A 001953, UK Publ. No. 2274284.

The mixture of products obtained from the CPO step enters a slurry reactor "B" for methanol synthesis The catalytic system in the slurry reactor was prepared by using CuCl and MeONa as precursors, by operating according to the procedures disclosed in EP-375,071. The copper salt and the alkali metal alkoxide were charged to the reactor under a nitrogen blanketing atmosphere. The solvent was then added (90 ml of thoroughly dried anisole) in the presence of methanol (40 mmol). The molar concentration of alkoxyde was kept at round 2M, the concentration of copper salt was 0.06M. During the step of process start-up, the reactor is pressurized and conditioned at 15 atm with a mixture of CO and $H_2$ ($H_2$:CO=2:1 by vol/vol) and the temperature is increased up to 100° C. before the reaction mixture coming from the CPO reactor enters it. In Table 1, the data of composition of the product mixtures in both reaction steps are reported.

The conversion rate of synthesis gas in methanol synthesis step is of 90% and selectivity to methanol is of 98%. The productivity of the system is limited by the methanol synthesis step and therefore resulted to be of 65 g of MeOH/h*litre of reactor volume.

EXAMPLE 2

In this case, the synthesis gas production passage was carried out at 1.5 MPa in the reactor "A" at the temperature of 750° C., on a monolithic catalyst which contains Rh and Ru. The reactants mixture (GHSV=300,000 $h^{-1}$) contained methane and oxygen in a mutual ratio of $O_2$:$CH_4$=0.29:0.71. The step of hydrogenation of carbon monoxide to yield methanol in the presence of unreacted methane was carried out by causing the reacted stream to flow through the slurry reactor at 1.0 MPa and at a temperature of 95° C.

The monolithic catalyst was obtained by dipping an enbloc alumina body into an aluminum hydroxide solution. A layer of hydroxide coats the enbloc body and, after drying and calcination, is converted into a porous hydroxide layer. After this treatment, the surface area of the monolithic body resulted to be of 12 $m^2/g$ (this process is referred to in pertinent technical literature as a "wash-coating" process). The monolithic body was soaked in a hydrocarbonaceous solution of $Rh_4(CO)_{12}$ and $Ru_3(CO)_{12}$ (hexane, Rh:Ru:Ir= 0.1:0.5:0.5, by mol/mol) for 2 hours. Under these conditions, reactions of dissociative chemisorption of the clusters take place, yielding to coating the surface of the monolithic body with a monolayer of noble metals, as it was verified by performing the quantitative analysis of the resulting metal contents (0.08% Rh, 0.4% Ru, 0.3% Ir).

The catalyst for the reactions of methanol syntheses was prepared by blending CuCl (6 mmol), $CH_3ONa$ (80 mmol), methyl formate (50 mmol) with 90 ml of anisole. The experiments were carried out according to the same operating procedures as disclosed in above Example 1; the obtained results are reported in Table 2.

The syn gas conversion in methanol synthesis step was of 92% and the selectivity to methanol was of 98%.

EXAMPLE 3

The synthesis gas production reactions were carried out in reactor "A" over a catalytic bed under a pressure of 3.0 MPa, GHSV=400,000 $h^{-1}$, outlet T 750° C., $O_2$:$CH_4$=0.41 (by vol/vol). The resulting synthesis gas, containing more than 10% of unreacted methane, was used in a second reactor (B) to perform F-T reactions of hydrocarbon synthesis. The pressure inside reactor "B" was kept at 3 MPa, the temperature at 300° C.

In CPO synthesis a monolithic catalyst was used which was prepared according to the same procedure as disclosed in Example 2. The catalyst for F-T synthesis was prepared by means of successive impregnations up to incipient wetness, of a gamma-alumina (surface area 150 $m^2/g$). The first impregnation was carried out with an aqueous solution of cobalt nitrate. After drying at 115° C., the catalyst was submitted to a second impregnation with an aqueous solution of ruthenium nitrate and then was submitted to a second drying procedure. A third impregnation step was carried out with an aqueous solution of potassium carbonate. After a further drying, the catalyst was calcined up to 350° C. The end catalyst contained 18% cobalt, 2.5% ruthenium, 1% potassium. The catalytic test was preceded by a thermal reduction treatment at 350° C., during which through reactors "A" and "B" a nitrogen gas stream containing 25% hydrogen was flown. The compositions of the reaction mixtures and of the roducts from both reaction step are reported in Table 3.

EXAMPLE 4

The same procedures as disclosed in Example 3 were repeated by using the same catalyst for the CPO reactions and, respectively, the same catalyst for F-T synthesis reactions; however, in this case the mixture of methane and oxygen fed to the CPO reactor "A" inlet contained a ratio of $O_2$:$CH_4$=0.55. The results obtained are reported in Table 4.

EXAMPLES 5–7

The experiments disclosed in Examples 1, 2 and 4 were repeated by using, as catalyst, in the first CPO reactor, a platinum-rhodium wire mesh, containing 10% by weight of rhodium. Said mesh has similar characteristics as of the wire meshes used in ammonia oxidations into nitric acid and is constituted by metal wires of 0.076 mm of diameter. Inasmuch as rhodium proved to be particularly active for CPO reactions and particularly inert in coal formation reactions, the meshes were modified by depositing on their surface, by electrochemical way, a layer of rhodium metal, from an aqueous solution of rhodium nitrate. The resulting material proved to be active in CPO reactions carried out under UHSV conditions, with selectivities for CO and $H_2$ higher than 95% under the same reaction conditions as disclosed in Examples 1–4, but with a lower selectivity to formaldehyde. In following Tables 5, 6 and 7, the results are reported which relate to the first reaction step in which the synthesis gas mixtures are obtained.

EXAMPLE 8

In this case, during the first pass of syn gas production, the same catalysts as of Example 2 were used, but with reactants mixtures containing $CH_4$:$O_2$:$CO_2$=1:0.5:0.5; whereas, during the following step of F-T synthesis, the catalyst disclosed in Example 3 was used. In the CPO step, the following process conditions were used: GHSV=400,000 $h^{-1}$, P=3 MPa, reactor outlet T=750° C. In the F-T synthesis reactor, the following reaction conditions were used: GHSV=1500 $h^{-1}$, P=3 MPa, T 300° C. The results obtained are reported in Table 8.

TABLE 1

| | OPC INLET (Molar fractions) | OPC OUTLET (Molar fractions) | MeOH OUTLET (Molar fractions) |
|---|---|---|---|
| $CH_4$ | 0.800 | 0.250 | 0.336 |
| $O_2$ | 0.200 | — | — |
| $H_2$ | — | 0.460 | 0.067 |
| CO | — | 0.240 | 0.032 |
| HCHO | — | 0.050 | — |
| $CH_3OH$ | — | — | 0.553 |
| $C_2ox+$ | — | — | 0.004 |
| DME | — | — | 0.001 |
| MF | — | — | 0.007 |

(DME = dimethyl ether; MF = methyl formate)

TABLE 2

|  | OPC INLET (Molar fractions) | OPC OUTLET (Molar fractions) | MeOH OUTLET (Molar fractions) |
|---|---|---|---|
| $CH_4$ | 0.710 | 0.077 | 0.190 |
| $O_2$ | 0.29 | — | — |
| $H_2$ | — | 0.562 | 0.111 |
| CO | — | 0.281 | 0.054 |
| HCHO | — | 0.080 | — |
| $CH_3OH$ | — | — | 0.627 |
| $C_2ox+$ | — | — | 0.004 |
| DME | — | — | 0.002 |
| MF | — | — | 0.012 |

TABLE 3

|  | OPC INLET (Molar fractions) | OPC OUTLET (Molar fractions) | F-T OUTLET (Molar fractions) |
|---|---|---|---|
| $CH_4$ | 0.710 | 0.075 | 0.117 |
| $O_2$ | 0.290 | — | — |
| $H_2$ | — | 0.570 | 0.394 |
| CO | — | 0.285 | 0.224 |
| HCHO | — | 0.070 | — |
| $CO_2$ | — | — | — |
| $H_2O$ | — | — | 0.207 |
| $C_2+$ | — | — | 0.058 |

TABLE 4

|  | OPC INLET (Molar fractions) | OPC OUTLET (Molar fractions) | F-T OUTLET (Molar fractions) |
|---|---|---|---|
| $CH_4$ | 0.666 | 0.015 | 0.013 |
| $O_2$ | 0.334 | — | — |
| $H_2$ | — | 0.590 | 0.394 |
| CO | — | 0.290 | 0.224 |
| HCHO | — | 0.080 | — |
| $CO_2$ | — | 0.010 | 0.008 |
| $H_2O$ | — | 0.015 | 0.215 |
| $C_2+$ | — | — | 0.058 |

TABLE 5

|  | OPC INLET (Molar fractions) | OPC OUTLET (Molar fractions) |
|---|---|---|
| $CH_4$ | 0.800 | 0.250 |
| $O_2$ | 0.200 | — |
| $H_2$ | — | 0.240 |
| CO | — | 0.480 |
| HCHO | — | 0.030 |
| $CO_2$ | — | — |
| $H_2O$ | — | — |

TABLE 7

|  | OPC INLET (Molar fractions) | OPC OUTLET (Molar fractions) |
|---|---|---|
| $CH_4$ | 0.666 | 0.001 |
| $O_2$ | 0.334 | — |
| $H_2$ | — | 0.300 |
| CO | — | 0.600 |
| HCHO | — | 0.080 |
| $CO_2$ | — | 0.009 |
| $H_2O$ | — | 0.010 |

TABLE 8

|  | OPC INLET (Molar fractions) | OPC OUTLET (Molar fractions) | F-T OUTLET (Molar fractions) |
|---|---|---|---|
| CH4 | 0.500 | 0.031 | 0.109 |
| $O_2$ | 0.250 | — | — |
| $H_2$ | — | 0.485 | 0.106 |
| CO | — | 0.303 | 0.160 |
| HCHO | — | 0.030 | — |
| $CO_2$ | 0.250 | 0.106 | 0.187 |
| $H_2O$ | — | 0.045 | 0.374 |
| $C_2+$ | — | — | 0.064 |

We claim:

1. Process of catalytic partial oxidation of natural gas to obtain synthesis gas and formaldehyde comprising the steps of:

oxidizing natural gas to synthesis gas and formaldehyde with a catalyst at an operating temperature, pressure and space velocity, wherein said catalyst comprises one or more metals selected from the Platinum group, said catalyst being in the shape of a wire mesh or being supported by a carrier, said carrier being made of inorganic compounds, wherein the weight percent of said metal or metals per total weight of catalyst and carrier is 0.1 to 20% and, said operating temperature is 300°–950° C., and said pressure is 0.5–50 atm, and said space velocity is 300,000–1,500,000 $h^{-1}$.

2. Process of claim 1, further comprising the steps of:

separating formaldehyde from said synthesis gas and reacting said synthesis gas by means of a catalyst to yield methanol, wherein where said methanol is synthesized by a high-conversion-per-pass synthesis, $CO_2$ and $H_2O$ are separated from said synthesis gas, the operating temperatures and pressures of said high-conversion-per-pass synthesis being 40°–200° C. and greater than 1 MPa, respectively, or where said methanol is synthesized by a conventional synthesis, the operating temperatures and pressures of said conventional synthesis being 200°–350° C. and greater than 1 MPa, respectively.

3. Process according to claim 1, in which the temperatures are comprised within the range of from 500° to 850° C., the pressure is within the range of from 1 to 40 atm and the space velocity is within the range of 400,000–1,500,000 $h^{-1}$.

4. Process according to claim 1, in which the percent by weight of metal or metals from Platinum Group is comprised within the range of from 0.1 to 5% by weight, based on total catalyst and carrier weight.

5. Process according to claim 1, in which the metals from Platinum Group are selected from rhodium, ruthenium and iridium.

6. Process according to any one of claims 3, 4, 5 or 1 wherein the molar ratio of $O_2$:$CH_4$ is lower than 0.5.

* * * * *